United States Patent
Porro et al.

(10) Patent No.: US 7,220,882 B2
(45) Date of Patent: May 22, 2007

(54) PROCESS FOR UREA PRODUCTION AND PLANT

(75) Inventors: Lino Porro, Novedrate (IT); Pasquale Gueli, Pigra (IT)

(73) Assignee: Urea Casale S.A. (CH)

( * ) Notice: Subject to any disclaimer, the term of this patent is extended or adjusted under 35 U.S.C. 154(b) by 0 days.

(21) Appl. No.: 11/407,746

(22) Filed: Apr. 17, 2006

(65) Prior Publication Data
US 2006/0247471 A1 Nov. 2, 2006

(30) Foreign Application Priority Data
Apr. 19, 2005 (EP) .................................. 05008437

(51) Int. Cl.
*C07C 273/04* (2006.01)
(52) U.S. Cl. ............................ 564/72; 564/66; 564/67; 564/68; 564/69; 564/70; 564/71
(58) Field of Classification Search .................. 564/66, 564/67, 68, 69, 70, 71, 72
See application file for complete search history.

(56) References Cited

U.S. PATENT DOCUMENTS

| 3,527,799 A | 9/1970 | Mavrovic |
| 4,613,696 A * | 9/1986 | Zardi ........................... 564/67 |
| 6,342,632 B1 | 1/2002 | Pagani et al. |

FOREIGN PATENT DOCUMENTS

| EP | 0 157 448 A1 | 10/1985 |
| WO | WO 00/00466 A | 1/2000 |

* cited by examiner

*Primary Examiner*—Peter O'Sullivan
(74) *Attorney, Agent, or Firm*—Akerman Senterfitt

(57) ABSTRACT

In a process for urea production of the type comprising the reaction between ammonia and carbon dioxide in a high-pressure reactor followed by an autothermal stripping of the resulting reaction mixture so as to obtain a gaseous flow comprising ammonia and carbon dioxide and a liquid flow comprising urea and residual carbamate in aqueous solution and by a stripping of said gaseous flow in units operating at medium pressure, a gaseous flow coming from said units operating at medium pressure and comprising ammonia and carbon dioxide is partially condensed in a condenser to give a mixed liquid/gaseous flow. The uncondensed gases comprising ammonia and carbon dioxide are separated from the liquid phase in a separator and subjected to washing in a packed portion of a column in countercurrent with a flow of a carbonate solution obtaining a gaseous flow essentially consisting of ammonia and a liquid flow comprising a carbamate solution in which the carbon dioxide contained in said uncondensed gases has been absorbed.

This process allows an effective recovery of ammonia without carbon dioxide for the recycling to the synthesis reactor.

8 Claims, 3 Drawing Sheets

PROCESS FOR UREA PRODUCTION AND PLANT

FIELD OF APPLICATION

In its most general aspect, the present invention concerns urea production.

In particular, the present invention concerns a process and a related plant for urea production of the type comprising the steps of:

carrying out a reaction between ammonia and carbon dioxide in a high-pressure reactor obtaining a reaction mixture comprising urea, carbamate and unreacted ammonia in aqueous solution, subjecting said reaction mixture to an autothermal stripping treatment in a decomposition unit of the carbamate obtaining a first gaseous flow comprising ammonia and carbon dioxide and a first liquid flow comprising urea and residual carbamate in aqueous solution, recycling said first gaseous flow comprising ammonia and carbon dioxide to said reactor, subjecting said first liquid flow to a stripping treatment in at least one carbamate decomposition unit operating at medium pressure of a urea recovery section, obtaining a second gaseous flow comprising ammonia and carbon dioxide and a second liquid flow comprising urea.

PRIOR ART

As is well known, urea synthesis from ammonia and carbon dioxide substantially takes place through two reactions: a first reaction in which carbamate is produced and a second reaction in which the carbamate just produced is decomposed into urea and water.

On an industrial scale, the aforementioned reactions are carried out in a reactor operating at high pressure (160–240 bar) of a synthesis section of a plant for urea production. From such a reactor, the urea is normally obtained in the form of an aqueous solution comprising carbamate, unreacted ammonia and carbon dioxide and possible inert gases previously introduced into the reactor.

The synthesis section of a urea plant also comprises a whole series of apparatuses in particular for the separation of the urea and for recycling carbamate and unreacted ammonia and carbon dioxide, the structure and function of which can considerably vary according to the technologies used for the urea synthesis.

Normally, the aqueous solution at the outlet of the reactor is treated in suitable carbamate decomposition units operating at high pressure (just like the reactor) from which an aqueous solution comprising urea and residual carbamate, intended to be treated in a urea recovery section, and a gaseous flow comprising ammonia, carbon dioxide and possible inert gases, intended to be recycled to the reactor in the suitable manner (direct or indirect) are obtained.

Regarding this, the present invention refers to the autothermal stripping treatments, in other words to those treatments in which the decomposition of the carbamate in the high-pressure units is carried out with the supply of heat without the help of stripping gases.

In the urea recovery section, the aforementioned solution comprising urea and residual carbamate is normally treated in one or more carbamate decomposition units operating at medium pressure (16–18 bar).

An aqueous solution, even richer in urea, and a gaseous flow comprising mainly ammonia and carbon dioxide and, in a very small part, steam and inert gases thus comes out from this (these) decomposition unit(s).

Now it is well-known that, in order to achieve an acceptable urea production yield, it may be important to subject the aforementioned gaseous flow at the outlet of the carbamate decomposition units operating at medium pressure to rectification distillation, so as to recover ammonia to then recycle it to the synthesis reactor. This is of particular importance for those technologies in which the urea synthesis is carried out with considerable excess of ammonia.

Regarding this, a suitable process and a related suitable apparatus for the rectification distillation of gaseous flows coming from carbamate decomposition units operating at medium pressure are thus normally provided in the urea production plant.

Such a process generally comprises the steps of:

a) partial condensation of a gaseous flow comprising ammonia, carbon dioxide, steam and inert gases coming from carbamate decomposition units operating at medium pressure in a condenser through mixing of said gaseous flow with a flow of a recycling carbonate solution, to form a carbamate solution containing a certain amount of the aforementioned uncondensed gases, b) separation of ammonia from said carbamate solution still containing a certain amount of the aforementioned uncondensed gases in a ammonia recovery column through bubbling of said carbamate solution with the uncondensed gases in a washing liquid and simultaneous washing with a descending flow of ammonia, obtaining a gaseous flow essentially consisting of ammonia and inert gases and a liquid flow comprising carbamate, c) recycling of said liquid flow comprising carbamate to the synthesis section of the urea production plant.

With the term "carbonate solution", in the field of the industrial urea production one means a diluted carbamate solution (for example 40–42% NH3, 8–10% CO2), particularly recycled, for example a diluted carbamate solution coming from the section operating at low pressure of the urea plant.

Although the conventional process described above for the rectification distillation of gaseous flows coming from carbamate decomposition units operating at medium pressure substantially achieves its purpose, it has different drawbacks in relation to the ammonia recovery column that are examined in greater detail hereafter.

First of all, the absorption of uncondensed carbon dioxide coming from the condenser is carried out by mixing with bubbling of the uncondensed gases in the washing liquid. This generally involves a poor absorption efficiency of the carbon dioxide in the washing liquid, which can only be improved by providing to considerably raise the level of washing liquid in the ammonia recovery column (to about 4–5 meters).

Moreover, during the transitions and above all in start-up step of the urea production plant, there is often a need to treat large amounts of uncondensed gases coming from the condenser in the ammonia recovery column. In this circumstance, it is very difficult to make the uncondensed carbon dioxide become completely absorbed in the washing liquid so that the unabsorbed carbon dioxide is transported upwards by the gaseous flow ascending in the column disadvantageously resulting in the formation of incrustations of carbamate through dry reaction with the ammonia of the flow descending in the column. Such incrustations of carbamate can obstruct both the column, particularly when they form at the level of plates provided in it, and the tubes of the condensers of the ammonia recovered from the column, if the transportation of carbon dioxide is such as to continue also outside of the column.

Moreover, it should be noted that the bubbling of the carbamate solution containing the gases not condensed in the washing liquid is carried out through a suitable distributor arranged in said liquid. Such a distributor is normally placed as low as possible, near to the bottom of the column so as to exploit the maximum available height of the washing liquid column for the absorption of the uncondensed carbon dioxide.

However, by doing so, substantially all of the washing liquid is aerated through bubbling and rising in it of the uncondensed gases introduced in the column and this makes the level of the washing liquid unstable and the measurement thereof uncertain. Moreover, during the transitions and above all in start-up step of the urea production plant, the washing liquid is in a turbulent state to the point that the level thereof can reach the lowest plate of the column, clogging it up.

The turbulence in the liquid can also make the operation of the pump for the recycling of the liquid flow comprising carbamate at the outlet of the column unstable.

In some cases there may even be a transportation of uncondensed gases coming from the condenser towards the liquid flow comprising carbamate at the outlet of the column. This makes the operation of the quoted pump for recycling said liquid flow comprising carbamate to the urea synthesis section even more problematic.

In light of the aforementioned drawbacks, the ammonia recovery process and related apparatus considered above are also scarcely flexible in use.

Indeed, to reduce as much as possible the transportation of uncondensed gases in the carbamate solution at the outlet of the column it is not possible to increase the temperature of the uncondensed gases at the inlet of the column and consequently the temperature of the carbamate solution, to be recycled to the synthesis section, this temperature therefore not being greater than 80–85° C.

The technical problem underlying the present invention is that of providing a process and a related plant for urea production that overcomes the aforementioned drawbacks concerning the rectification distillation of a gaseous flow coming from medium pressure carbamate decomposition units.

SUMMARY OF THE INVENTION

Such a problem is solved according to the present invention by a process for urea production of the type comprising the steps of:
  carrying out a reaction between ammonia and carbon dioxide in a high-pressure reactor obtaining a reaction mixture comprising urea, carbamate and unreacted ammonia in aqueous solution,
  subjecting said reaction mixture to an autothermal stripping treatment in a decomposition unit of the carbamate obtaining a first gaseous flow comprising ammonia and carbon dioxide and a first liquid flow comprising urea and residual carbamate in aqueous solution,
  recycling said first gaseous flow comprising ammonia and carbon dioxide to said reactor,
  subjecting said first liquid flow to a stripping treatment in at least one carbamate decomposition unit operating at medium pressure of a urea recovery section, obtaining a second gaseous flow comprising ammonia and carbon dioxide and a second liquid flow comprising urea, characterized in that it also comprises the following steps:
  carrying out a partial condensation of said second gaseous flow comprising ammonia and carbon dioxide in a condenser to give a mixed liquid/gaseous flow consisting of a carbamate solution and uncondensed gases comprising ammonia and carbon dioxide,
  separating said mixed liquid/gaseous flow in a separator to give a third liquid flow substantially consisting of carbamate in aqueous solution and a third gaseous flow consisting of said uncondensed gases,
  washing said third gaseous flow consisting of said uncondensed gases in a column having a packed portion, said washing being carried out in said packed portion in countercurrent with a flow of a carbonate solution, obtaining a fourth gaseous flow essentially consisting of ammonia and a fourth liquid flow comprising a carbamate solution in which the carbon dioxide contained in said uncondensed gases has been absorbed.

The present invention also concerns a plant for carrying out the aforementioned process. Such a plant for urea production comprises:
  a urea synthesis reactor operating at high pressure to carry out a reaction between ammonia and carbon dioxide obtaining a reaction mixture comprising urea, carbamate and unreacted ammonia in aqueous solution,
  a carbamate decomposition unit operating at high pressure to carry out an autothermal stripping treatment on said reaction mixture obtaining a first gaseous flow comprising ammonia and carbon dioxide and a first liquid flow comprising urea and residual carbamate in aqueous solution,
  means for recycling said first gaseous flow comprising ammonia and carbon dioxide to said reactor,
  at least one carbamate decomposition unit operating at medium pressure to subject said first liquid flow to a stripping treatment, obtaining a second gaseous flow comprising ammonia and carbon dioxide and a second liquid flow comprising urea,
  and it is characterized in that it comprises:
  a condenser for the partial condensation of said second gaseous flow to give a mixed liquid/gaseous flow consisting of a carbamate solution and uncondensed gases comprising ammonia and carbon dioxide,
  a separator for carrying out the separation of said mixed liquid/gaseous flow in a separator to give a third liquid flow substantially consisting of carbamate in aqueous solution and a third gaseous flow consisting of said uncondensed gases,
  a column having a packed portion for the washing therein of said third gaseous flow consisting of said uncondensed gases in countercurrent with a flow of a carbonate solution, obtaining a fourth gaseous flow essentially consisting of ammonia and a fourth liquid flow comprising a carbamate solution in which the carbon dioxide contained in said uncondensed gases has been absorbed.

The characteristics and the advantages of the present invention shall become clearer from the following description of some preferred embodiments made with reference to the figures attached hereto and provided for indicating and not limiting purposes.

BRIEF DESCRIPTION OF THE DRAWINGS

In the figures.

DETAILED DESCRIPTION

In order to simplify the description of the present invention, in the figures just a part of a urea plant is shown and in particular the apparatuses used for the rectification distillation of gaseous flows coming from carbamate decomposition units operating at medium pressure are schematically shown, the rest of the urea plant not being significant for understanding the present invention.

Figure 1:
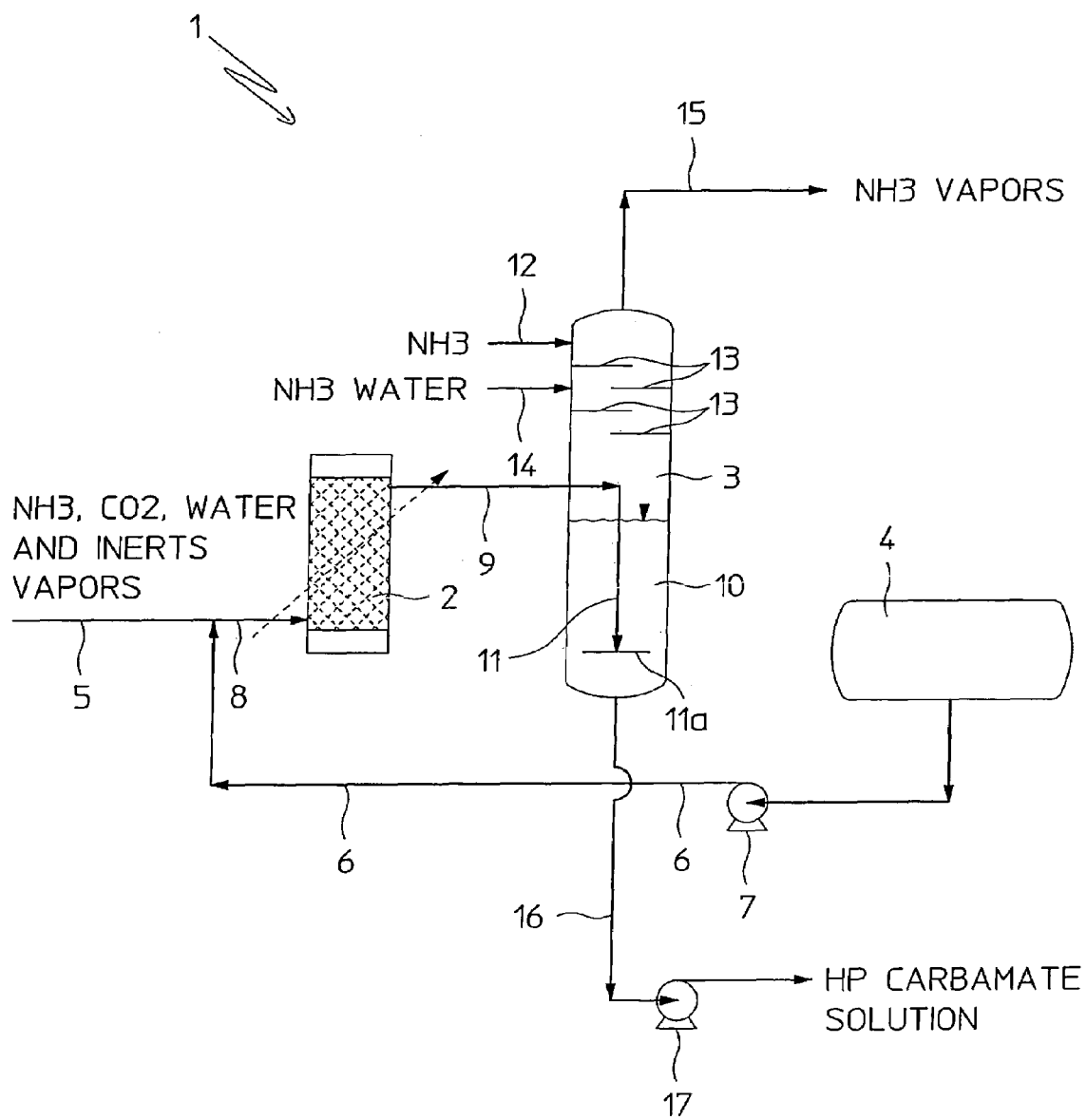
FIG. 1 schematically illustrates a part of a conventional urea plant for the rectification distillation of a gaseous flow coming from carbamate decomposition units operating at medium pressure of a urea production plant, FIG. 2 schematically illustrates a part of a urea plant according to an embodiment of the invention for the rectification distillation of a gaseous flow coming from carbamate decomposition units operating at medium pressure of a urea production plant, FIG. 3 schematically illustrates a part of a urea plant according to another embodiment of the invention for the rectification distillation of a gaseous flow coming from carbamate decomposition units operating at medium pressure of a urea production plant.

With reference to FIG. 1, a conventional urea plant, globally indicated with 1, comprises a condenser 2, an ammonia recovery column 3 and a reservoir 4 containing a recycling carbonate solution.

The flow line 5 indicates a gaseous flow comprising ammonia, carbon dioxide, steam and inert gases coming from a carbamate decomposition unit operating at medium pressure (about 17–20 bar).

Such a gaseous flow 5 is combined with a liquid flow 6 of a carbonate solution coming from the reservoir 4 through a pump 7.

The flow line 8 represents a mixed liquid/gaseous flow obtained from the mixing of the liquid flow 6 consisting of the aforementioned carbonate solution with the gaseous flow comprising ammonia, carbon dioxide, steam and inert gases.

The mixed liquid/gaseous flow 8, which shall normally have a pressure of about 17–20 bar, is sent to the condenser 2 where most of the carbon dioxide, ammonia and steam originally contained in the gaseous flow 5 condense to form a carbamate solution.

The flow line 9 represents a flow of said carbamate solution at the outlet of the condenser 2 still containing a certain amount of uncondensed gases comprising ammonia, carbon dioxide, steam and inert gases.

The carbamate solution 9 mixed with the uncondensed gases is sent to the ammonia recovery column 3.

The column 3, under normal operating conditions, contains a predetermined level of washing liquid 10, consisting of the carbamate solution itself, in which the flow 9 consisting of the carbamate solution mixed with the uncondensed gases coming from the condenser 2 is made to flow, through a descending duct 11.

In particular, conventional technology provides that the descending duct 11 inferiorly ends with a distributor 11a submerged in the washing liquid 10 through which the carbamate solution 9 mixed with the uncondensed gases is sprayed into the washing liquid 10.

In such a way the washing liquid 10 is constantly crossed from the bottom towards the top by gas bubbles, thus being aerated.

The operation of the column 3 is such as to substantially absorb the uncondensed carbon dioxide coming from the condenser 2 from the remaining uncondensed gases, particularly from the ammonia.

Regarding this, the uncondensed carbon dioxide is substantially absorbed in the washing liquid 10 inside the column 3 through the mixing of the flow 9, consisting of the carbamate solution and the uncondensed gases, with said liquid 10 and with a flow 12 of liquid ammonia (at 40–45° C.) at the inlet of the column 3 above a plurality of plates 13 normally provided at different heights of the column 3.

In particular, the flow 12 of ammonia, having a lower temperature than the operating temperature of the column 3, allows the washing liquid 10 to be cooled thus promoting the absorption in said liquid 10 of the carbon dioxide introduced into the column 3 with the uncondensed gases.

The remaining uncondensed gases, including ammonia to be recovered, mixed with the washing liquid 10, rise in the column 3 meeting the plates 13 through which they are washed by droplets of liquid possibly transported in suspension.

Since it is always possible that the uncondensed gases rising in the column 3 may contain a certain amount of carbon dioxide not absorbed in the washing liquid 10, a flow 14 of a second washing liquid consisting of ammonia in aqueous solution normally coming from the washing section of the inert gases of the urea production plant is normally provided at the inlet of the column 3, at the height of intermediate plates 13.

In such a way, the lowest plates 13 are substantially freed from possible incrustations of carbamate that could form through reaction between carbon dioxide contained in the flow of uncondensed gases ascending in the column 3 and ammonia of the flow 12 descending in the column 3.

At the end of the treatment in the column 3 on one side a gaseous flow 15 superiorly coming out from the column and comprising ammonia, inert gases but essentially without carbon dioxide and, on the other side, a liquid, flow 16 inferiorly coming out from the column 3 consisting of an aqueous solution comprising carbamate are thus obtained.

The gaseous flow 15 containing the recovered ammonia is recycled into suitable condensers for the condensation of the ammonia whereas the liquid flow 16 is recycled through a pump 17 directly to the synthesis section of the urea production plant.

Figure 2:
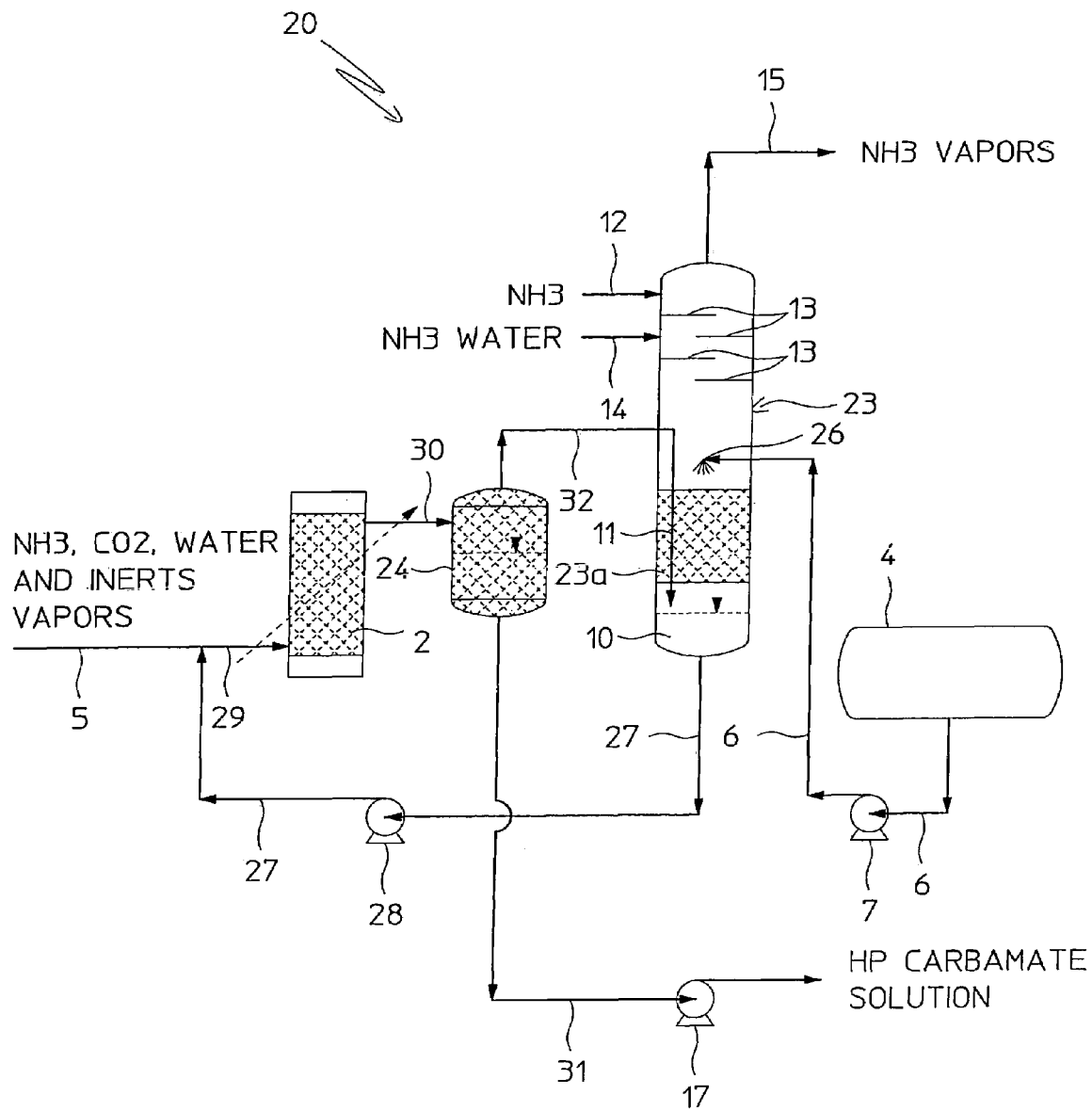

With reference to FIG. 2, a urea plant according to an embodiment of the invention is globally indicated with 20. In FIG. 2, to structural elements that are identical or equivalent from the functional point of view to those of the conventional urea plant of FIG. 1 described above, the same reference numerals shall be attributed and they shall not be described any further.

The urea plant 20 comprises a condenser 2, an ammonia recovery column 23 and a reservoir 4 containing a diluted carbonate solution.

In accordance with the present invention, the column 23 is packed in a lower portion thereof 23a of predetermined height with a standard packing capable of offering a large contact surface (for example pall or raschig rings).

Moreover, a flow 6 of carbonate solution coming from the reservoir 4 is fed superiorly to the packed portion 23a of the column 23 through a spray/injection distributor 26.

The aforementioned carbonate solution crosses the packed portion 23a of the column where it comes into contact with a gaseous flow comprising ammonia and carbon dioxide, for the absorption of carbon dioxide in the way that shall be described hereafter, obtaining a first carbamate solution. Such a first carbamate solution is kept at a constant level of liquid 10, below the packed portion 23a and the excess thereof constitutes a flow 27 going out from the bottom of the column 23.

Such a flow 27 going out from the column 23, through a pump 28, is combined with a gaseous flow 5 coming from carbamate decomposition units of a urea production plant operating at high pressure. The gaseous flow 5 comprises ammonia, carbon dioxide, steam and inert gases. The flow line 29 represents the liquid/gaseous mixture resulting from the mixing of the liquid flow 27 coming from the column 23 and of the gaseous flow 5 coming from the carbamate decomposition units operating at high pressure.

Such a mixture 29 is fed into the condenser 2 where most of the carbon dioxide, ammonia and steam originally contained in the gaseous flow 5 condense to form a second carbamate solution in which the carbamate concentration shall be higher.

The flow line 30 represents the aforementioned second carbamate solution mixed with the uncondensed gases at the outlet of the condenser 2. In accordance with another aspect of the present invention, such a second solution 30 of carbamate mixed with the uncondensed gases is fed into a separator 24 instead of directly to the ammonia recovery column 23.

In the separator 24 the carbamate solution is separated from the uncondensed gases. At the outlet of the separator 24 there shall thus be a liquid flow 31, consisting of the aforementioned carbamate solution substantially without uncondensed gases and a gaseous flow 32 comprising uncondensed ammonia and uncondensed carbon dioxide.

The liquid flow 31, through a pump 17, is recycled to the urea synthesis section whereas the gaseous flow 32 is sent to the ammonia recovery column 23.

In accordance with the present invention, the feed into the column 23 is achieved by means of a descending duct 11 passing through the packed portion 23a of the column 23.

The descending duct 11 also ends with a distributor (not shown) of the gaseous flow 32 above the level of liquid 10 inside the column 23.

In such a way, the uncondensed gases fed into the column 23 shall rise along it passing through the packed portion 23a where they can be effectively washed by the diluted carbamate solution coming from the reservoir 4 and by the flow 12 of liquid ammonia descending from the top of the column 23.

Such washing advantageously allows substantially the totality of the carbon dioxide to be absorbed into the diluted carbamate solution. Therefore, the gas coming out from the top end of the packed portion 23a shall mainly comprise ammonia and shall be substantially without carbon dioxide.

Such a gas, after further washing at the plates 13 of the column 23, comes out superiorly from the column 23 along the flow line 15 and is recovered in suitable condensers.

The process described above has numerous advantages with respect to the corresponding known processes.

The main advantage of the process according to the invention lies in the high carbon dioxide absorption efficacy in the carbonate solution. This is achieved thanks to the fact that the washing is carried out directly on the uncondensed gases in a packed portion of the recovery column with a flow in countercurrent of a carbonate solution. In virtue of the large surface for the liquid/gas contact/exchange offered by the packed portion of the column 3 and the high water content of the carbonate solution, the possibility that the carbon dioxide of the uncondensed gases is transported in the top part of the column, i.e. above the packed portion, is practically nullified even in overload conditions of the gaseous flow coming from the high pressure carbamate decomposition unit.

Advantageously, in the process according to the invention the transportation of liquid in the gaseous phase ascending in the column is also heavily reduced since the uncondensed gases are fed to the column without the liquid phase that accompanies them through a separator between the condenser and the recovery column.

Moreover, it should be noted that in the recovery column provided in the process according to the invention there is no bubbling of gas in a liquid phase. This advantageously makes the level of liquid inside the recovery column stable and easier to measure and promotes the correct operation of the pumps operating at high pressure for the recycling of carbamate in aqueous solution.

The urea plant 20 provided for the process according to the invention is also more flexible in the use with respect to the corresponding conventional apparatuses. Indeed, during the transitions and above all in the start-up step of the urea plant or in the case of increase of the temperature at the outlet of the condenser, the corresponding increase in carbon dioxide in the uncondensed gases is effectively absorbed in the recovery column.

Consequently, the carbamate in liquid phase at the outlet of the separator shall have a higher temperature (up to 100–105° C.) and this advantageously allows the urea synthesis section to make a significant recovery of heat.

A further advantage of the process according to the invention lies in the fact that it lends itself particularly to being implemented in pre-existing urea production plants. In particular, the modernization of these plants so as to implement the aforementioned process can be carried out at reasonable costs since the interventions to be brought to the recovery columns only concern their inside (packing, reconfiguration of pre-existing ducts and distributors) and do not involve any modification to the expensive shells resistant to the pressure of such columns.

Moreover, the addition of a pump and of the separator with respect to a conventional plant only slightly affects the overall cost of the plant or the intervention on the existing plant.

Figure 3:
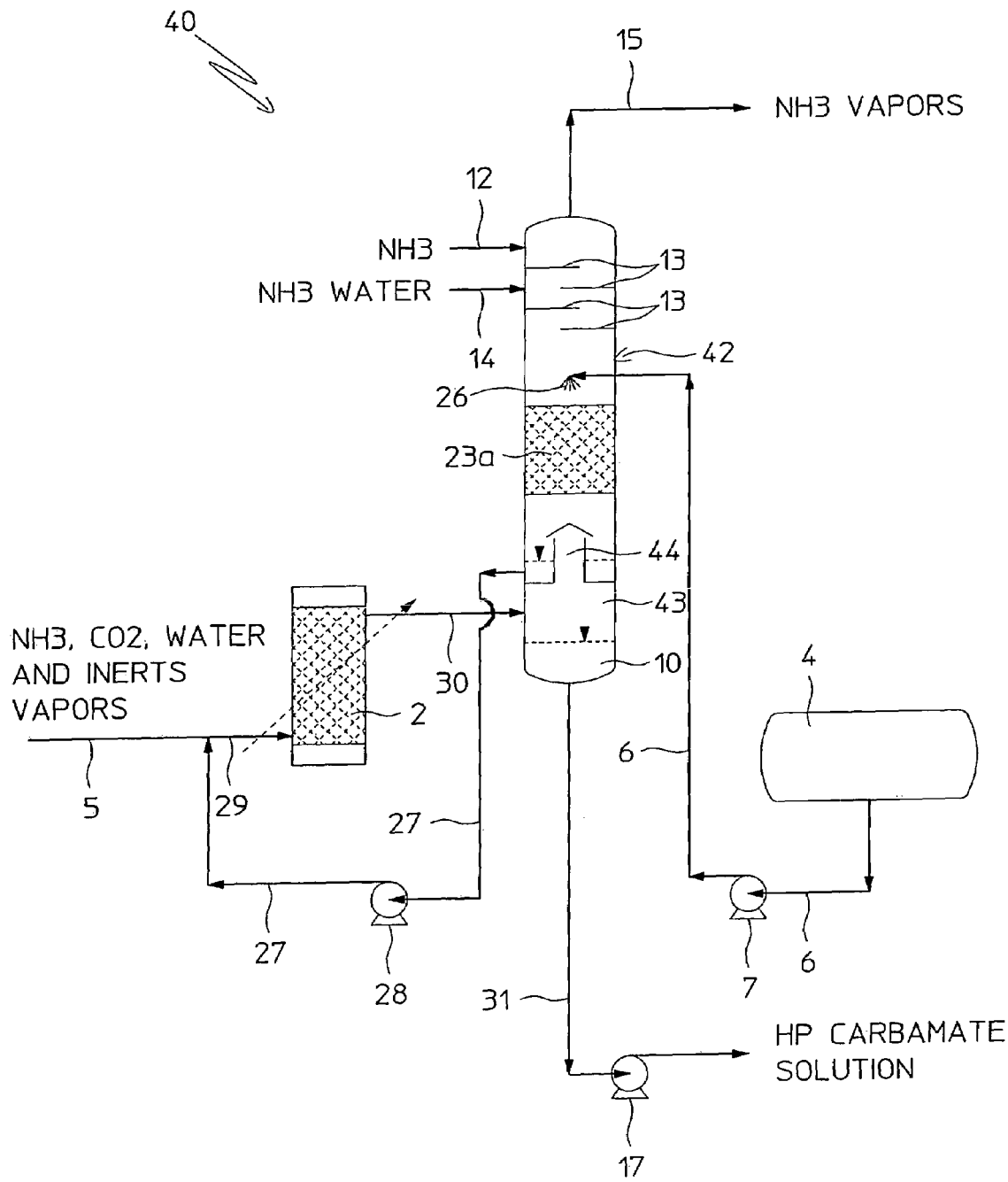

Now with reference to FIG. 3, a urea plant according to another embodiment of the invention is wholly indicated with 40. In FIG. 3 structural elements that are identical or equivalent from the functional point of view to those of the urea plant 20 already described previously with reference to FIG. 2 shall be attributed the same reference numerals and shall not be described any further.

In accordance with this embodiment of the invention, the urea plant 40 comprises a new column 42 tat with respect to the column 23 of the urea plant 20, is structured so as to have a liquid/gas separator 43 in a lower portion thereof below the packed portion 23a.

In such a way, the flow 30 of carbamate solution together with the uncondensed gases at the outlet of the condenser can be fed directly into the column 42 at the separator 43. One thus avoids the need for a liquid/gas separator outside the column.

Thus from the separator 43 on one side a flow 31 of carbamate solution that comes out from the bottom of the column 42 to then be recycled to the synthesis section is obtained and on the other side a flow of uncondensed gases that rises in the column is obtained.

Preferably, the separator 43 superiorly terminates with a substantially chimney-shaped plate 44 from which the flow of the uncondensed gases is fed into the central part of the column towards the packed portion 23a. Here, the uncondensed gases are washed, for the absorption of carbon dioxide, with a descending flow 6 of a carbonate solution coming from the reservoir 4 in the manner already described previously for the apparatus 20.

The washing liquid descending from the packed portion 23a collects on the bottom of the chimney-shaped plate 44 according to a predetermined level and goes out from the column 42 along the flow line 27 to then be mixed, with the help of a pump 28, with a gaseous flow 5 coming from carbamate decomposition units operating at medium pressure.

The urea plant 40 according to the invention has substantially the same advantages as the urea plant 20 already described previously.

In addition, the provision of a liquid/gas separator integrated in the column involves a significant reduction in the overall investment costs for making a urea production plant.

Of course, a man skilled in the art can bring numerous modifications and variants to the urea plants according to the invention described above in order to satisfy contingent and specific requirements, all of which are in any case covered by the scope of protection of the invention, as defined by the following claims.

The invention claimed is:

1. Process for urea production of the type comprising the steps of:
    carrying out a reaction between ammonia and carbon dioxide in a high-pressure reactor obtaining a reaction mixture comprising urea, carbamate and unreacted ammonia in aqueous solution,
    subjecting said reaction mixture to an autothermal stripping treatment in a decomposition unit of the carbamate obtaining a first gaseous flow comprising ammonia and carbon dioxide and a first liquid flow comprising urea and residual carbamate in aqueous solution,
    recycling said first gaseous flow comprising ammonia and carbon dioxide to said reactor,
    subjecting said first liquid flow to a stripping treatment in at least one carbamate decomposition unit operating at medium pressure of a urea recovery section, obtaining a second gaseous flow comprising ammonia and carbon dioxide and a second liquid flow comprising urea,
wherein it also comprises the following steps:
    carrying out a partial condensation of said second gaseous flow comprising ammonia and carbon dioxide in a condenser to give a mixed liquid/gaseous flow consisting of a carbamate solution and uncondensed gases comprising ammonia and carbon dioxide,
    separating said mixed liquid/gaseous flow in a separator to give a third liquid flow substantially consisting of carbamate in aqueous solution and a third gaseous flow consisting of said uncondensed gases,
    washing said third gaseous flow consisting of said uncondensed gases in a column having a packed portion, said washing being carried out in said packed portion in countercurrent with a flow of a carbonate solution, obtaining a fourth gaseous flow essentially consisting of ammonia and a fourth liquid flow comprising a carbamate solution in which the carbon dioxide contained in said uncondensed gases has been absorbed.

2. Process according to claim 1, wherein said uncondensed gases of said third flow are fed below said packed portion of the column and said washing carbonate solution is fed into the column above said packed portion.

3. Process according to claim 2, wherein said separator is outside said column and said feed of the unreacted gases is carried out through a duct that crosses said packed portion and terminates above a liquid kept at a substantially constant level in said column.

4. Process according to claim 2, wherein said separator is formed inside said column below said packed portion and superiorly terminates with a substantially chimney-shaped plate.

5. Process according to claim 4, wherein said feed of the unreacted gases is carried out by said chimney-shaped plate above a liquid kept at a substantially constant level that collects on the bottom of said plate.

6. Process according to claim 3, wherein said liquid consists of a portion of the carbamate solution of said fourth flow in which the carbon dioxide contained in said uncondensed gases has been absorbed.

7. Process according to claim 1, wherein it comprises the step of combining said fourth flow comprising a carbamate solution in which the carbon dioxide contained in said uncondensed gases has been absorbed with said second gaseous flow comprising ammonia and carbon dioxide coming from carbamate decomposition units operating at medium pressure.

8. Process according to claim 1, wherein it comprises the step of recycling said third liquid flow substantially consisting of carbamate in aqueous solution at the outlet of said separator to the synthesis section of the urea plant.

* * * * *